United States Patent
Thiele et al.

(10) Patent No.: US 9,170,184 B2
(45) Date of Patent: Oct. 27, 2015

(54) METHOD OF REGULATING THE VISCOSITY OF A MIXTURE COMPRISING AT LEAST TWO COMPONENTS HAVING DIFFERENT VISCOSITIES

(71) Applicant: BASF SE, Ludwigshafen (DE)

(72) Inventors: Kai Thiele, Antwerp (BE); Bart Janssen, Kalmthout (BE); Wouter Ducheyne, Antwerp (BE)

(73) Assignee: BASF SE, Ludwigshafen (DE)

( * ) Notice: Subject to any disclaimer, the term of this patent is extended or adjusted under 35 U.S.C. 154(b) by 197 days.

(21) Appl. No.: 13/792,432

(22) Filed: Mar. 11, 2013

(65) Prior Publication Data
US 2013/0240779 A1 Sep. 19, 2013

Related U.S. Application Data

(60) Provisional application No. 61/609,951, filed on Mar. 13, 2012.

(51) Int. Cl.
*G05D 11/12* (2006.01)
*G01N 11/00* (2006.01)
(Continued)

(52) U.S. Cl.
CPC .............. *G01N 11/00* (2013.01); *G05D 24/02* (2013.01); *C10G 73/34* (2013.01); *G01N 2011/0073* (2013.01)

(58) Field of Classification Search
CPC ....... C10G 73/34; G01N 11/00; G05D 24/00; G05D 11/12
USPC ............. 73/861; 203/1, 2; 202/150; 422/105, 422/127, 128
See application file for complete search history.

(56) References Cited

U.S. PATENT DOCUMENTS 3,025,232 A * 3/1962 Jones, Jr. ............... 208/347
4,452,265 A 6/1984 Lonnebring
(Continued)

FOREIGN PATENT DOCUMENTS

CN 2881601 Y 3/2007
EP 1 480 033 A1 11/2004
(Continued)

OTHER PUBLICATIONS

International Search Report and Written Opinion issued Jun. 26, 2013 in PCT/EP2013/054843 (with partial English language translation).

(Continued)

*Primary Examiner* — Nina Bhat
(74) *Attorney, Agent, or Firm* — Oblon, McClelland, Maier & Neustadt, L.L.P.

(57) ABSTRACT

A method of regulating the viscosity of a mixture containing at least two components having different viscosities, which includes the steps of:
  (a) determination of the viscosity of the mixture via ultrasound measurements,
  (b) standardization of the viscosity determined to standard conditions,
  (c) comparison of the standardized viscosity with a prescribed intended value, and
  (d) adjustment of the viscosity of the mixture by increasing or decreasing the proportion of at least one component of the mixture,
where the ultrasound measurements in step (a) are carried out at or in a line conveying the mixture or in a vessel.

13 Claims, 3 Drawing Sheets

(51) Int. Cl.
*G05D 24/02* (2006.01)
*C10G 73/34* (2006.01)

(56) References Cited

U.S. PATENT DOCUMENTS

| | | | |
|---|---|---|---|
| 7,578,171 B2* | 8/2009 | Manneville | 73/54.23 |
| 8,091,435 B2* | 1/2012 | Will et al. | 73/861.28 |
| 2004/0177679 A1 | 9/2004 | Lahaut | |
| 2007/0117997 A1 | 5/2007 | Keggenhoff et al. | |

FOREIGN PATENT DOCUMENTS

| | | |
|---|---|---|
| EP | 1 932 828 A2 | 6/2008 |
| FR | 2 091 976 A1 | 1/1972 |
| GB | 1 500 080 A | 2/1978 |
| WO | WO 2005/030841 A1 | 4/2005 |

OTHER PUBLICATIONS

International Preliminary Examination Report issued Aug. 1, 2014 in PCT/EP2013/054843 (with English translation of Category of Cited Documents).

* cited by examiner

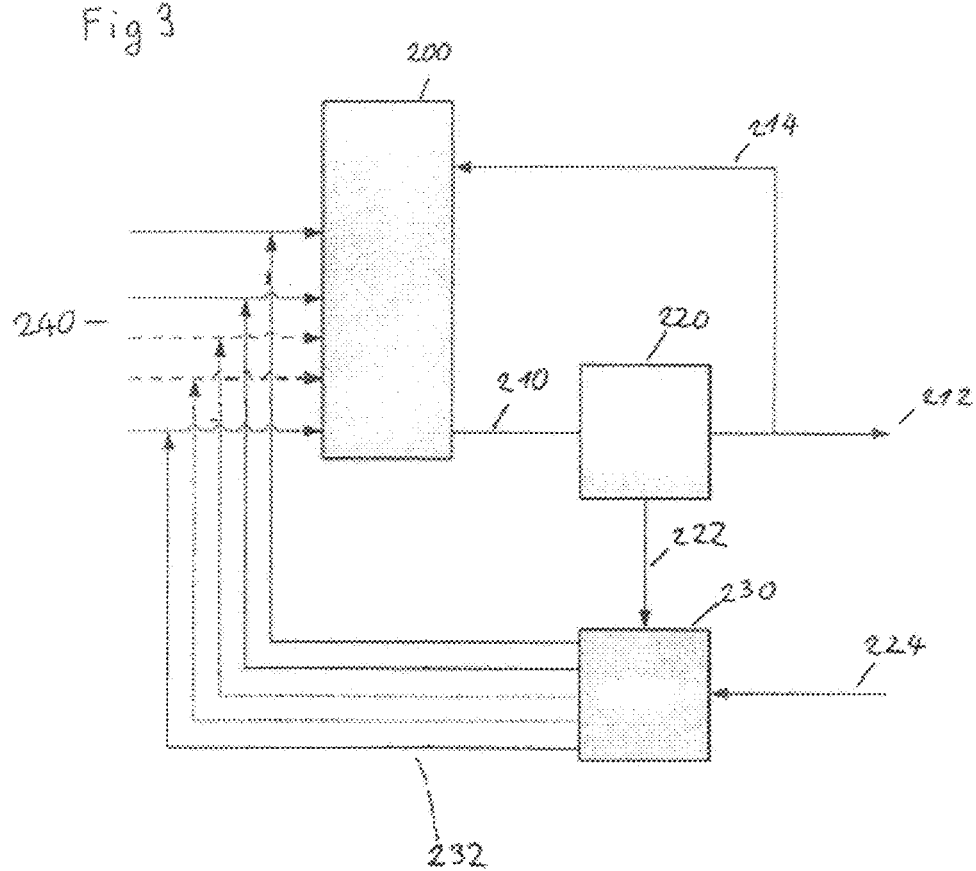

METHOD OF REGULATING THE VISCOSITY OF A MIXTURE COMPRISING AT LEAST TWO COMPONENTS HAVING DIFFERENT VISCOSITIES

The invention relates to a method of regulating the viscosity of a mixture comprising at least two components having different viscosities, in particular monomers and oligomers of the diphenylmethane diisocyanate (MDI) series.

In the preparation of a product composed of a plurality of components, the properties of the product are dependent on the mixing ratio of the components. Such mixtures are frequently formed as a result of one or more chemical reactions and the mixing ratio is dependent on the conditions prevailing during the reaction. Despite all efforts to keep the conditions during the reaction constant, variations occur every now and again with the consequence that the properties of the product obtained no longer correspond to the required properties.

For example, the synthesis of diaminodiphenylmethane (MDA) from aniline and formaldehyde by means of acid catalysis forms a mixture of 3 different isomers of the monomer (monomeric MDA) and also various long-chain oligomers. A mixture comprising crude diphenylmethane diisocyanates (crude MDI) is obtained from this crude MDA mixture by reaction of the crude MDA with phosgene. The crude MDI, too, is a mixture of 3 different isomers of the monomer (monomeric MDI) with various long-chain oligomers, with the ratio of the components to one another corresponding essentially to that of the crude MDA. A mixture of diphenylmethane diisocyanates (MDI) is obtained from the crude MDI and part of the monomers present in the starting mixture are separated off from this mixture of diphenylmethane diisocyanates. The residual fraction is an MDI mixture which comprises the oligomeric MDI and the residual monomeric MDI and is often referred to as "polymeric MDI". The polymeric MDI (PMDI) mixture is discharged from this separation stage to a tank farm. The monomeric MDI obtained can be separated into various monomeric MDI products in a further, subsequent separation stage (distillation or crystallization).

The proportion of monomeric MDI in the mixture is critical to the properties of the resulting PMDI mixture, in particular to its viscosity. The viscosity is increased by a decreasing proportion of monomeric MDI and decreases when the proportion of monomeric MDI increases.

To monitor the product properties, in particular the viscosity, samples are therefore taken regularly during production and are subsequently examined to determine their properties in the laboratory. If deviations from the intended properties are found, the parameters of the production process are adapted. A disadvantage of this procedure is that there is a considerable time interval between sampling and any required adaptation of the process during which time the production process cannot be regulated. If the deviations in the product properties found are too great, only unusable reject material is produced during this time. Continuous monitoring of the viscosity is therefore necessary in order to be able to guarantee constant product properties.

EP 1 480 033 A1 discloses a method and an apparatus for determining the isomer composition in isocyanate production processes. In the method disclosed, the composition of an isocyanate isomer mixture is determined by, for example, a spectrum of the isomer mixture being recorded on-line by means of near infrared spectroscopy, intermediate infrared spectroscopy or Raman spectroscopy using an optical sensor. The measured spectrum is then entered into a chemometric calibration model which has been set up beforehand for the mixture of these isomers. Evaluation of the spectrum in the chemometric calibration model gives the isomer concentrations in the isomer mixture. Comparison of the actual concentration of the isomers determined in this way with specified intended concentrations enables the isomer separation plant to be regulated accordingly.

A disadvantage of the method is that the chemometric model has to be calibrated afresh at the beginning by frequent sampling and analyses for each isomer mixture used. Furthermore, samples have to be continually taken and analyzed during later operation in order to optimize this statistical model. Even when only a small standard deviation results on average, large absolute deviations can occur in individual cases. As a result, the quantitative reliability of the spectroscopic instrument is not sufficiently great for effective monitoring of the process. The further continual sampling required and the sensitive sensors required result in a high maintenance requirement and incur increased risks and outlays in respect of occupational hygiene and environmental protection.

U.S. 2004/0177679 A1 discloses a rotational viscometer and a method of measuring the viscosity of a liquid. Here, the magnitude of the friction between the liquid and the rotating component is measured. The rotating part is driven by a motor and is in contact with the liquid, with a separation element separating the parts in contact with the liquid from the motor. As a result, a pressure above that of the liquid is built up on the motor side of the separation element. This is intended to prevent liquid from penetrating into the rotational viscometer.

CN 2881601 Y discloses an apparatus for measuring the viscosity of a liquid with temperature compensation. The measuring apparatus comprises a steel ball which moves in a glass tube, with the steel ball being braked by the liquid to be tested. The liquid is taken from a main line via a bypass line and introduced into the measuring apparatus. The movement of the steel ball is recorded via a proximity switch. In addition, the temperature is measured for correcting the measured values.

A disadvantage of these and further mechanical measurement methods is that they are susceptible to leakages and/or have to be sealed very well. Furthermore, the mechanical measuring elements are susceptible to blockages.

It is an object of the present invention to provide a method by means of which a prescribed intended viscosity of a mixture comprising at least two components having different viscosities can be ensured.

The object is achieved by a method of regulating the viscosity of a mixture comprising at least two components having different viscosities, which comprises the steps:
(a) determination of the viscosity of the product by means of ultrasound measurements,
(b) standardization of the viscosity determined to standard conditions,
(c) comparison of the standardized viscosity with a prescribed intended value,
(d) adjustment of the viscosity of the mixture by increasing or decreasing the proportion of at least one component of the mixture,
where the ultrasound measurements in step (a) are carried out at or in a line conveying the mixture or in a vessel.

The mixture whose viscosity is to be regulated is a mixture of at least two components having different viscosities, with the properties of the mixture, in particular the viscosity thereof, being dependent on the mixing ratio of the components. The components can be various isomers and/or various oligomers of a chemical compound. The mixture can be the result of a chemical reaction, with the conditions prevailing during the reaction having an influence on the mixing ratio of the components. The mixture can also be the product of a processing step by means of which components are added or withdrawn from the mixture. Furthermore, the mixing ratio can change during storage due to further reactions occurring.

In the first step (a) of the method, the viscosity of the mixture is determined. This is effected by means of ultrasound measurements at or in a line conveying the mixture or in a vessel accommodating the mixture. The ultrasound measuring device used can be installed directly on a line conveying the mixture, for example on a flange of a pipe, with a measuring probe of the ultrasound measuring device projecting into the mixture. It is likewise possible to take off part of the mixture from the line via a bypass and feed this to the measuring device. When the viscosity of the mixture is measured in a vessel, the measuring device is preferably installed on a wall of the vessel or integrated into the latter.

In the subsequent step (b) of the method, the measured value determined in the first step (a) is standardized to standard conditions. The standard conditions comprise a prescribed standard temperature. For this purpose, the temperature of the mixture comprising at least two components is measured and is used together with a model for standardization to the standard temperature. As standard temperature, a temperature in the range from, for example, 20° C. to 50° C. is selected. Good results can be obtained using even a simple model which provides a proportionality factor B and a temperature correction factor y:

$$U_{25°C} = B^{-1} \cdot Q \cdot (T/25)^y \quad \text{(I)}$$

Here, $U_{25°C}$ is the viscosity standardized to a temperature of 25° C., Q is the measured viscosity and T is the measured temperature. The proportionality factor B and the temperature correction factor y are determined by analysis of some samples of the mixture in the laboratory and subsequent curve fitting.

With an additional constant, the model can be used in another temperature unit, for example in kelvin:

$$U_{298K} = B^{-1} \cdot Q \cdot ((T+A)/273.14)^y \quad \text{(II)}$$

The constant A, the proportionality factor B and the temperature correction factor y are determined by analysis of some samples of the mixture in the laboratory.

In the third method step (c), the measured viscosity value standardized to standard conditions is compared as actual value with a prescribed intended value. If actual value and intended value differ from one another, the viscosity of the mixture is adjusted in the last step (d) of the method by changing the mixing ratio of the individual components relative to one another. This is achieved by increasing or decreasing the proportion of at least one component of the mixture.

In an embodiment of the method, the mixture composed of a plurality of components is obtained from a crude mixture by distillation or crystallization, with at least one component being at least partly separated off. Here, the viscosity of the mixture obtained by distillation or crystallization is determined by means of ultrasound measurements in the outflow stream.

The adjustment of the viscosity in step (d) of the method is then effected, for example, by increasing or decreasing the amount separated off of the at least one component separated off by distillation or crystallization. A further variant for adjusting the viscosity is mixing in of a partial amount of the at least one component separated off by distillation or crystallization.

If the crude mixture is the result of a production process, the adjustment of the viscosity in step (d) of the method can be achieved by changing the composition of the crude mixture by changing the process parameters of the production process.

Depending on the embodiment of the method of the invention, it is conceivable to use not only the three above-described possibilities for adjusting the viscosity but also a combination of a plurality of these possibilities. Furthermore, it is possible to carry out the adjustment of the viscosity in such a way that the amount of the at least one component separated off or the amount of the mixture obtained by distillation or crystallization is constant.

An example of a mixture comprising at least two components having different viscosities is diisocyanatodiphenylmethane (MDI). The preparation of MDI is carried out in a plurality of stages. In the first stage, diaminodiphenylmethane (MDA) is synthesized from aniline and formaldehyde by means of acid catalysis. The crude MDA obtained in this way is a mixture of 3 different isomers of the monomer (monomeric MDA) and various long-chain oligomers.

In the second stage of the production process, phosgene is synthesized from carbon monoxide and chlorine and is reacted in the third stage with the crude MDA from the first stage in a solvent to give crude MDI. Monochlorobenzene or dichlorobenzene is generally used as solvent.

The crude MDI, too, is a mixture of 3 different isomers of monomeric MDI with various long-chain oligomers, with the ratio of the components to one another corresponding essentially to that of the crude MDA. A mixture of diphenylmethane diisocyanates (MDI) is obtained from the crude MDI by separating off part of the monomeric MDI comprised in the starting mixture by means of distillation under reduced pressure. The remaining MDI mixture comprising the oligomeric MDI and the residual proportion of monomeric MDI is referred to as "polymeric MDI" (PMDI) and is discharged from this separation step into a storage tank. The monomeric MDI obtained is separated in a further, subsequent separation stage, for example distillation or crystallization, into various MDI products. The main products are 4,4'-MDI having a purity of about 98% and a mixture of 2,4'- and 4,4'-MDI having a mixing ratio of about 50:50, with the latter and the PMDI mixture remaining after the distillation comprising small amounts of 2,2' isomer.

The proportion of monomeric MDI is critical to the properties of the PMDI mixture obtained in this way, in particular its viscosity. The viscosity is increased by a decreasing proportion of monomeric MDI and is reduced when the proportion of monomeric MDI is increased.

The viscosity of the PMDI mixture accordingly depends on how much monomeric MDI is separated off in the distillation. This is in turn dependent on the process conditions and the original composition of the crude MDI. In addition, secondary reactions as a result of which the proportion of monomeric MDI decreases and the viscosity increases occur during storage of fresh MDI.

If the method of the invention is used in a process in which a PMDI mixture is obtained by separation of monomeric MDI from a crude MDI mixture by means of distillation, the viscosity is preferably determined by ultrasound measurements on the outflow stream of the product.

By means of the measured viscosity values standardized to standard conditions, it is possible to carry out regulation so that the measured actual value approximates a prescribed intended value.

Such regulation can be effected by changing the process parameters in the distillation so that the amount of monomeric MDI separated off from the crude MDI mixture is regulated as a function of the viscosity determined. This can be effected, for example, by regulating the energy or heat introduced.

Regulation can also be carried out by mixing part of the monomeric MDI separated off by distillation back into the PMDI mixture, with the amount mixed in being dependent on the measured and standardized actual viscosity and the prescribed intended viscosity of the MDI mixture.

Furthermore, the composition of the crude MDI mixture can be regulated as a function of the viscosity determined. Since the isomer composition of the crude MDI corresponds essentially to that of the original crude MDA, this can be achieved by adjustment of the process conditions in the MDA synthesis. For example, the proportion of the isomers in the crude MDA mixture can be influenced by changing the ratio of aniline to formaldehyde and/or the amount of acid catalyst used.

Depending on the embodiment of the method of the invention, it is possible to use one of the three abovementioned regulation approaches or a combination of a plurality of the regulation approaches described. If the amount of crude MDA introduced is kept constant and the composition of the crude MDA mixture does not change, the amounts of monomeric MDI separated off and remaining PMDI mixture varies. Additional regulation of the crude MDA composition and/or the amount of crude MDA introduced enables the ratio of the PMDI mixture produced to the amount of monomeric MDI separated off to be influenced in addition to the viscosity of the PMDI mixture.

A further example of the use of the method of the invention arises from the fact that the viscosity of freshly produced MDI mixture increases over the storage time. The cause of this effect is secondary reactions which occur in the mixture and lead to the formation of relatively long-chain oligomers having a higher viscosity. However, this results in the stored mixture no longer having the properties required in the particular case.

According to the invention, it is proposed that the viscosity of a mixture comprising at least two components having different viscosities be regulated by changing its composition, with the measurement of the viscosity of the mixture being carried out on a line between a vessel comprising the mixture composed of at least two components and a dispensing device.

The composition of the mixture stored in the vessel can then be changed as a function of the measured standardized viscosity. This can be brought about, for example, by introduction of a further mixture, with a mixture having a higher viscosity than the mixture stored in the storage tank being added in the case of the viscosity of the mixture in the vessel being too low and a mixture having a lower viscosity than the mixture stored in the vessel being added in the case of the viscosity of the mixture in the vessel being too high.

In the case of a PMDI mixture as mixture comprising at least two components having different viscosities, freshly produced PMDI is introduced into a vessel in which PMDI is stored, with the viscosity of the freshly produced product optionally being influenced by changing the intended value for the viscosity in production. This intended value is in turn selected so that the viscosity of the PMDI stored in the vessel approximates the viscosity desired on dispensing.

If the PMDI mixture introduced into the vessel is obtained by removal of monomeric MDI by means of distillation or crystallization, the method of the invention can be cascaded. In this case, the viscosity of a freshly produced PMDI mixture is regulated in a first stage by one of the above-described methods and the viscosity of a PMDI mixture stored in a vessel is set by means of this in a second stage. Here, the actual and intended values of the second stage are used to calculate the intended value for the viscosity in the first stage. The intended value of the second stage is the viscosity required at the dispensing device, and the actual value of the viscosity in the second stage is measured at the connecting line between the vessel and the dispensing device. The actual value in the first stage is the viscosity measured at a connecting line between the apparatus in which the fresh PMDI mixture is obtained and the vessel. The intended value in the first stage is the intended value for the viscosity of the fresh PMDI mixture introduced into the vessel and is accordingly set as a function of the actual viscosity measured at the connecting line between the vessel and the dispensing device. Furthermore, the intended viscosity required for the dispensed PMDI mixture also goes into the calculation of the intended value in the first stage. This concatenation of the viscosity regulation in production and storage produces a fresh PMDI mixture whose actual viscosity is suitable for approximating the viscosity of the PMDI mixture stored in the vessel to the actual viscosity required at the dispensing device.

In an embodiment of the method of the invention, the mixture comprising at least two components having different viscosities is stored in at least two vessels, with the mixing ratio of the components of the mixture relative to one another being different in the respective vessels. Here, it is provided that the mixture be dispensed from the vessels via a dispensing device, that the mixture from the individual vessels be mixed in a mixing device before dispensing and the viscosity of the mixture be determined by means of ultrasound measurements at a connecting line between the mixing device and the dispensing device. The choice of the mixing ratio then determines the viscosity of the dispensed mixture. The mixing device can be a static mixer, a further vessel or a storage tank connected via appropriate pipes to the individual vessels and the dispensing plant. Apart from measuring the viscosity of the mixture, it is also possible to measure the viscosities of the mixtures stored in the various vessels by means of additional measuring devices. These additional measuring devices are, for example, arranged directly in the vessels or on the appropriate connecting lines.

Since in the case of PMDI as mixture comprising at least two components having different viscosities the progressive increase in the viscosity results from a decrease in the content of monomeric MDI, monomeric MDI is stored in at least one further vessel in addition to the stored PMDI in an embodiment of the method of the invention. In this way, monomeric MDI can be mixed in in a mixing device as a function of the measured viscosity of the mixture before dispensing of the PMDI. The viscosity measurement is preferably carried out by means of ultrasound on a connecting line to the dispensing plant.

In the above-described cases, a further storage tank or a static mixer as described, for example, in WO 2005 030841 serves, for example, as mixing device.

BRIEF DESCRIPTION OF THE DRAWINGS

The invention is illustrated below with the aid of the drawings and the following description. The drawings show:

FIG. 3: a schematic depiction of the regulation of the viscosity in the mixing or storage of isomers.

FIG. 1 shows the regulation scheme of a separation of isomers with regulation of the viscosity.

Figure 1:
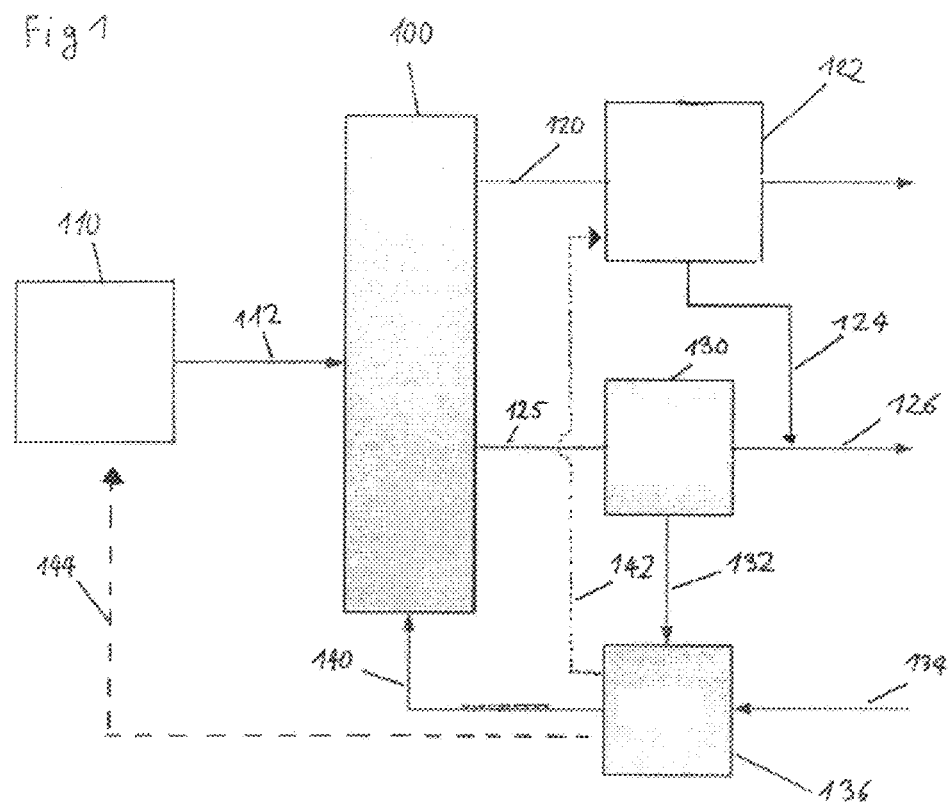
FIG. 1: a schematic depiction of the regulation of the viscosity in the separation of isomers.

The crude material 112 is introduced into a separation apparatus 100 in which at least one component 120 is separated off in its entirety or partly. The remaining mixture 125 flows from the separation apparatus 100 to an outflow 126. The viscosity of the remaining mixture 125 is dependent on how much of the at least one component 120 is still comprised in the mixture 125. A viscosity measuring device 130 is arranged between the separation apparatus 100 and the outflow 126. The measuring device 130 determines the viscosity of the mixture 125 by means of ultrasound. The measured viscosity is standardized to standard conditions by the measuring device 130. The temperature and optionally the mass flow of the mixture 125 are taken into account for the standardization. The standardized viscosity is entered as actual viscosity 132 into a regulator 136. In the regulator 136, the actual viscosity is compared to a prescribed intended viscosity 134. When the actual viscosity differs from the intended viscosity, one or more control signals 140, 142, 144 are generated, depending on the embodiment. The process parameters of the separation apparatus 100 are influenced by means of the control signal 140 and the amount of the at least one component 120 separated off is thus controlled. The control signal 142 controls a regulating valve 122 via which part of the at least one component 120 which has been separated off can be mixed into the mixture 125. If a mixture of at least two components 120 which is separated further in a subsequent process step is separated off, proportions of one or more of the separated components 120 can also be mixed into the mixture 125. The process parameters in the production 110 of the crude material are influenced by means of the control signal 144, resulting in the composition of the crude material changing. It is likewise possible to control the amount of introduced raw material 112 by means of the control signal 144.

In the case of PMDI production, the production 110 of the crude material is the synthesis of crude MDI and the separation apparatus 110 is, for example, configured as a distillation apparatus.

If the method of the invention is used in a process in which the mixture comprising at least two components having different viscosities is a mixture obtained by separation of monomeric MDI from a crude MDI mixture by means of distillation, the viscosity is preferably determined by ultrasound measurements on the outflow stream of the product. Here, the monomeric MDI is the component 120 which is separated off and comprises a mixture of the various isomers of monomeric MDI.

The viscosity of the PMDI mixture is determined by means of a viscosity measuring device 130 configured as ultrasonic measuring device in the line leading to the oufflow 126, with a temperature compensation and optionally a compensation for the mass flow also being carried out in the viscosity measuring device 130. Regulation can then be carried out by means of the regulator 136 using the measured viscosity values 132 standardized to standard conditions so that the measured actual viscosity 132 approximates a prescribed intended viscosity 134.

Such regulation can be carried out via the regulating signal 140 by changing the process parameters in the distillation 100 so that the amount of monomeric MDI mixture 120 separated off from the crude MDI mixture 112 is regulated as a function of the measured viscosity 132. This can be effected, for example, by regulating the heat or energy introduced.

Regulation can also be effected by mixing part of the monomeric MDI 120 which has been separated off by distillation back into the PMDI mixture 125 by means of a valve 122, with the amount to be mixed in being dependent on the measured and standardized actual viscosity 132 and the prescribed intended viscosity 134 of the PMDI mixture and being transmitted to the valve 122 via the regulating signal 142. Part of one or more components of the monomeric MDI mixture 120 which is fractionated further in a subsequent process step can also be introduced into the PMDI mixture 125 according to the same principle.

Furthermore, the amount and composition of the crude MDI mixture 112 can be regulated via the control signal 144 as a function of the measured actual viscosity 132. Since the isomer composition of the crude MDI mixture 112 corresponds essentially to that of the crude MDA obtained as intermediate, this can be achieved by adjustment of the process conditions in the MDA synthesis. Here, the proportion of monomers in the crude MDA mixture can, for example, be influenced by changing the ratio of aniline to formaldehyde and/or the amount of acid catalyst used.

Depending on the embodiment of the method of the invention, it is possible to use one of the three abovementioned regulating approaches alone or else a combination of a plurality of the regulating approaches described.

Figure 2:
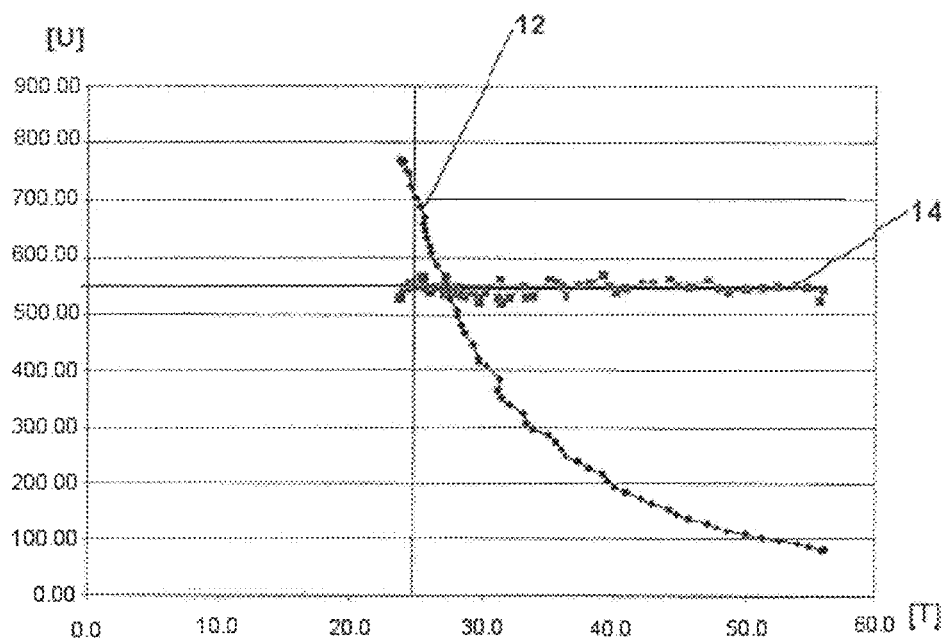
FIG. 2: the standardization of ultrasonic viscosity measurements to standard conditions.

In FIG. 2, a measurement of the viscosity of MDI is shown as a function of the temperature with and without standardization.

In the graph shown in FIG. 2, the viscosity of an MDI sample is plotted against the temperature. Here, the Y axis shows the viscosity [U] and the temperature [T] is plotted on the X axis, with the X axis comprising a temperature range from 0° C. to 60° C. The curve 12 shows the measured viscosity of the sample. The measured point at a temperature of 25° C. is used to standardize the viscosity of the sample to standard conditions. The result of the standardization is shown as curve 14 in the graph.

FIG. 3 shows the regulating scheme for regulation of the viscosity in the storage or dispensing of a mixture comprising at least two components having different viscosities.

Before the mixture comprising at least two components having different viscosities is dispensed via the dispensing line 212, its viscosity is determined by means of an ultrasonic measuring device 220. The measured viscosity of the mixture is standardized to standard conditions by the measuring device 220. The actual viscosity 222 standardized to standard conditions is compared with a prescribed intended viscosity 224 in a regulator 230. If the actual viscosity 222 differs from the intended viscosity 224, one or more regulating signals 232 by means of which the introduction of one or more mixtures 240 into the mixing device 200 is controlled are generated.

In the case of PMDI as mixture comprising at least two components having different viscosities, the regulator 230 can regulate the introduction of freshly produced PMDI into a mixing device 200 configured as a tank as a function of the deviation of the actual viscosity 222 from the intended viscosity 224 via a regulating signal 232. Here, the viscosity of the freshly produced PMDI can optionally be influenced by changing the intended value for the viscosity in the production process.

If a plurality of different MDI mixtures having different viscosities are available, the ratio in which the various MDI mixtures are introduced into the mixing device 200 can be set via the regulator 230. Since the progressive increase in the viscosity of a PMDI mixture results from a decrease in the content of monomeric MDI, monomeric MDI is, in an embodiment of the method of the invention, stored in at least one further storage tank in addition to the stored PMDI mixture. In this way, monomeric MDI can be mixed in in a mixing device 200 as a function of the measured actual viscosity 222 of the mixture via the regulating signal 232 before dispensing of the PMDI mixture.

In a variant of the method, the viscosity of the mixture comprising at least two components having different viscosities can be determined in a mixing device 200 configured as a tank without dispensing the mixture. For this purpose, the mixture is conveyed via the line 210 past the ultrasonic measuring device 220 and goes back into the tank 200 via the return line 214.

LIST OF REFERENCE NUMERALS

[U] Viscosity
[T] Temperature
12 Viscosity
14 Standardized viscosity
100 Separation apparatus
110 Crude MDI production
112 Crude material
120 Component separated off (monomeric MDI)
122 Valve
124 Recirculated 2-ring MDI
125 Remaining mixture
126 Outflow (PMDI mixture)
130 Viscosity measuring device
132 Actual viscosity
134 Intended viscosity
136 Regulator
140 Control signal for separation (distillation/crystallization)
142 Control signal for recirculation
144 Control signal for MDI production
200 Mixing device
212 Dispensing line
214 Return line
220 Measuring device
222 Actual viscosity
224 Intended viscosity
230 Regulator
232 Regulating signal
240 Mixture

The invention claimed is:

1. A method of regulating the viscosity of a mixture comprising at least two components having different viscosities, the method comprising:
   (a) determining the viscosity of the mixture via ultrasound measurements;
   (b) standardizing the viscosity determined to standard conditions;
   (c) comparing the standardized viscosity with a prescribed intended value; and
   (d) adjusting the viscosity of the mixture by increasing or decreasing a proportion of at least one component of the mixture,
   wherein the ultrasound measurements in the determining (a) are carried out at or in a line conveying the mixture or in a vessel,
   wherein
   the mixture comprising at least two components having different viscosities comprises monomeric diphenylmethane diisocyanates and oligomeric diphenylmethane diisocyanates,
   the mixture comprising a plurality of components is obtained from a crude mixture by distillation or crystallization, with a component being at least partly separated off,
   and wherein the crude mixture is obtained from a production process in which the crude mixture is obtained from a crude diaminodiphenylmethane mixture by a process comprising reacting the crude diaminodiphenylmethane with phosgene and changing the composition of the crude diaminodiphenylmethane mixture by changing the process parameters of the production process in order to adjust the viscosity in the adjusting (d).

2. The method according to claim 1, wherein the viscosity of the mixture obtained by distillation or crystallization is determined via ultrasound measurements in the outflow stream.

3. The method according to claim 1, wherein the adjustment of the viscosity (d) is effected by increasing or decreasing the amount separated off of the component separated off by distillation or crystallization by changing the introduction of energy or removal of energy.

4. The method according to claim 1, wherein the adjustment of the viscosity (d) is effected by mixing in a partial amount of the component separated off by distillation or crystallization or by mixing in a crude product mixture having a different composition.

5. The method according to claim 1, wherein the adjustment of the viscosity (d) is carried out such that the amount of the component separated off or the amount of the mixture obtained by distillation or crystallization is constant.

6. The method according to claim 1, wherein the mixture comprising at least two components having different viscosities is stored in a vessel and can be dispensed via a dispensing device and the measurement of the viscosity of the mixture in the determining (a) of the method is carried out at a connecting line between the vessel and the dispensing device.

7. The method according to claim 6, wherein, when the viscosity of the mixture stored in the vessel is too low, the viscosity is increased by introducing a mixture having a higher viscosity than the mixture stored in the vessel and when the viscosity of the mixture stored in the vessel is too high, the viscosity is reduced by introducing a mixture having a lower viscosity than the mixture stored in the vessel.

8. The method according to claim 7, wherein two regulations are cascaded, with the viscosity of a fresh mixture fed to the vessel being regulated in a first stage by a method comprising:
   (a) determining the viscosity of the mixture via ultrasound measurements,
   (b) standardizing the viscosity determined to standard conditions;
   (c) comparing the standardized viscosity with a prescribed intended value; and
   (d) adjusting the viscosity of the mixture by increasing or decreasing a proportion of at least one component of the mixture,
   wherein the ultrasound measurements in the determining (a) are carried out at or in a line conveying the mixture or in a vessel, the viscosity of the mixture stored in the vessel being set in a second stage by the fresh mixture, with the viscosity measured at the connecting line between the vessel, and
   the dispensing device and the intended value of the viscosity in the second stage being taken into account in the calculation of the intended value in the first stage.

9. The method according to claim 1, wherein the mixture comprising at least two components having different viscosities is stored in at least two vessels and can be dispensed via a dispensing device, with the mixing ratio of the components of the mixture to one another being different in the respective vessels, and the mixture from the individual vessels is mixed in a mixing device before dispensing and the viscosity of the mixture is determined by ultrasound measurements at a connecting line between the mixing device and the dispensing device, with the viscosity of the dispensed mixture being set by selection of the mixing ratio.

10. The method according to claim 9, wherein a further vessel or a static mixer is employed as the mixing device.

11. The method according to claim 1, wherein the monomeric diphenylmethane diisocyanates are at least partly separated off from the mixture during the distillation or crystallization.

12. The method according to claim 1, wherein the ultrasound measurement in the determining (a) is carried out by measurement of the radiation losses of an ultrasonic probe surrounded by the mixture.

13. The method according to claim 1, wherein measurement deviations due to a mixture temperature deviating from the standard conditions are compensated in the standardization (b) of the viscosity determined to standard conditions.

\* \* \* \* \*